United States Patent [19]

Suhr

[11] 4,152,379
[45] May 1, 1979

[54] ANESTHESIA HUMIDIFIER

[75] Inventor: Manfred W. Suhr, Cottage Grove, Wis.

[73] Assignee: Airco, Inc., Montvale, N.J.

[21] Appl. No.: 800,757

[22] Filed: May 26, 1977

[51] Int. Cl.² .................. B01F 3/04; A61M 15/00
[52] U.S. Cl. .................................. 261/142; 128/193;
 261/62; 261/64 R; 261/119 R; 261/120;
 261/DIG. 65
[58] Field of Search ............... 261/64 R, 64 B, 64 D,
 261/119 R, 120, 81, 122–124, 142, DIG. 65, 62,
 65; 55/122; 128/185–187, 192–194

[56] References Cited

U.S. PATENT DOCUMENTS

| | | | |
|---|---|---|---|
| 557,086 | 3/1896 | Schroeder | 261/120 X |
| 1,069,335 | 8/1913 | Johnson | 261/120 |
| 1,411,950 | 4/1922 | Wyatt | 261/120 |
| 1,447,336 | 3/1923 | Baughman | 261/120 X |
| 1,550,057 | 8/1925 | Beeler | 261/120 |
| 2,862,354 | 12/1958 | Barnhart | 55/122 |
| 3,045,990 | 7/1962 | Kennan, Jr. | 261/120 |
| 3,334,819 | 8/1967 | Olavson | 261/124 X |
| 3,608,834 | 9/1971 | MacLaren | 261/124 X |
| 4,051,205 | 9/1977 | Grant | 261/DIG. 65 |

Primary Examiner—Richard L. Chiesa
Attorney, Agent, or Firm—Roger M. Rathbun; Edmund W. Bopp; Larry R. Cassett

[57] ABSTRACT

A gas humidifying device is disclosed which includes a generally enclosed chamber defining a water reservoir, and an umbrella-shaped member positioned in the chamber with its downwardly facing peripheral edge normally extending beneath the surface of the water in the reservoir, whereby the interior of said member defines a gas accumulation space in contact with the water surface. Gas inlet means are connected to the gas accumulation space for introducing a dry gas to be humidified; and gas outlet means are connected to the chamber, and communicate with the chamber which is external to the gas accumulation space within the umbrella-shaped member. At least portions of the peripheral edge of the umbrella-shaped member are upwardly displaceable from the normal position to a position above the water surface and such displacements intermittently occur as pressure builds up in the gas accumulation space in consequence of gas flow proceeding to such space from the inlet means. Such displacements of the member peripheral edge above the water surface enable intermittent flow of gas past the member edge, where intimate gas-water contact is effected, with the humidified gas then proceeding to the gas outlet means. The displacements of the peripheral edge also serve to agitate the water and surface thereof, which promotes uniformity of temperature of water in the reservoir—which reservoir may be provided with heating means to maintain the water temperature at an elevated temperature. The unbrella-shaped member can be mounted to be vertically displaceable as a unit; or the member can be constrained against unit movement, but possess sufficient flexibility to enable elastic upward displacement of the peripheral edge to a position above the water level, with the displacements of the periphery occurring uniformly or by sections.

6 Claims, 3 Drawing Figures

4,152,379

ANESTHESIA HUMIDIFIER

BACKGROUND OF INVENTION

This invention relates generally to gas treatment apparatus, and more specifically relates to apparatus for humidifying an anesthetic or other gas which is to be furnished to a patient in the course of medical treatment.

In the course of various medical procedures, gases, which may include anesthetic agents, are administered to patients undergoing treatment. In order to insure maximum salutary effects, it is desirable, if not necessary, to humidify such gas prior to furnishing same to the patient. Accordingly, various techniques for humidifying these gases are commonly utilized in the medical arts, and numerous devices have long been employed for such purposes.

While many of such prior art devices are quite effective for the cited function of humidification, such prior devices are often unduly complex and of commensurate high cost to manufacture.

Furthermore, the principles upon which much of the prior apparatus is based, are such as to generate relatively high back pressure during operation of same. While in principle it is thus desirable for the pressure drop across such devices to be relatively small—so that a patient's breathing might operate such device in a closed circuit—many of these prior devices have not enabled such an operation except by the introduction of additional and complex control elements.

In accordance with the foregoing, the present invention provides a gas humidifying device suitable for use in humidifying anesthetic gases or the like, which operates on simple and dependable principles, and which is of commensurate low cost to manufacture and which further provides simple, dependable, and highly effective apparatus for use in humidifying anesthetic gases and the like, creating very low back pressure in the gas circuit and therefore is operable by a patient's breath in a closed circuit.

Summary of Invention

The gas humidifying device of the present invention includes a generally enclosed chamber defining a water reservoir, and an umbrella-shaped member positioned in the chamber with its downwardly facing peripheral edge normally extending beneath the surface of the water in the reservoir, whereby the concave interior of said member defines a gas accumulation space in contact with the water surface.

Gas inlet means are connected to the gas accumulation space for introducing a dry gas, such as an anesthetic-carrying gas which is intended to be humidified. Gas outlet means are connected to the chamber, and communicate with the chamber space which is external to the gas accumulation space contained beneath the umbrella-shaped member. At least portions of the peripheral edge of the umbrella-shaped member are upwardly and self-restorably displaceable from the aforementioned normal position. Such upward displacements intermittently occur as positive differential pressure builds up in the gas accumulation space (in comparison to the chamber space) as a result of gas flow proceeding to the inlet and raise the peripheral edge above the surface of the water. These displacements of the peripheral edge of the umbrella-shaped member above the water surface enable intermittent flow of gas past the member edge, where intimate gas-water contact is effected, after which the humidified gas proceeds through the chamber to the gas outlet means and thence to the patient.

The displacements of the peripheral edge of the umbrella-shaped member, serve the function of agitating the water and surface thereof, which promotes uniformity of temperature in the reservoir as well as achieve a good gas/water interface to humidify the gas. This is an important consideration in apparatus of the present type, in that such apparatus is preferably provided with underlying heating means, for introducing heat into the water contained therein. In the absence of such agitation, the water in the reservoir tends to become layered into zones of differing temperatures.

The umbrella-shaped member can be mounted as to be vertically displaceable as a unit; or the member can be constrained against unit movement, but possess sufficient flexibility to enable periodic upward displacement of the peripheral edge above the water level, the displacements of the peripheral edge either occurring uniformly or by sections thereof.

BRIEF DESCRIPTION OF DRAWINGS

The invention is diagrammatically illustrated, by way of example, in the drawing appended hereto, in which.

Description of Preferred Embodiment

Figure 1:
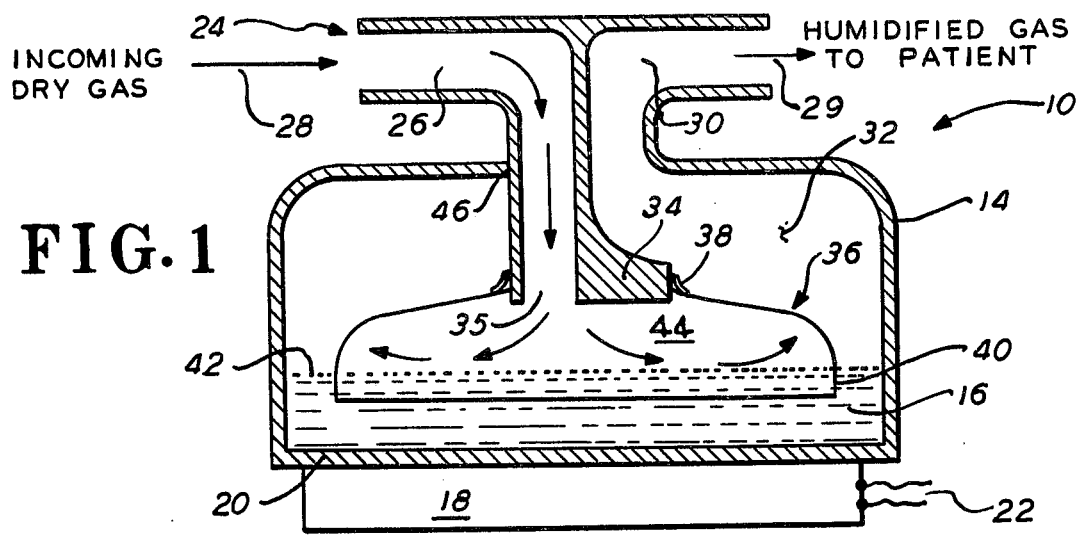
FIG. 1 is a longitudinal cross-sectional view illustrating a first embodiment of apparatus in accordance with the present invention.

In FIG. 1 herein, a longitudinal cross-sectional view appears, which is schematic in nature, of apparatus 10 in accordance with the present invention. Apparatus 10 is in general terms a humidifying device appropriate for use in introducing water vapor and thus humidifying a dry gas or gases flowed through the depicted device. Apparatus 10 is, however, particularly applicable for use in humidifying gases or mixtures of gases which are combined with and carry an anesthetic agent, the objective therefore being one of humidifying such gas or gas mixture which is thereupon to be furnished to a patient in the course of medical treatment.

Apparatus 10 includes a generally enclosed chamber 14, which chamber serves to define a container for a water reservoir 16 which is deposited therein. In a preferable form of the present apparatus, an electric heater 18 of conventional design, underlies and is in good thermal contact with the bottom wall 20 of chamber 14. Electrical power for heater 18 is provided from power lines, as at 22. Heating means 18 provides heat flow into the water reservoir 16; the objective of such heating is to facilitate transfer of water vapor to the gas being humidified, and in some instances to partially modify the temperature of the gas ultimately to be furnished to the patient. It may be observed here that one of the problems encountered where heating is effected in the fashion illustrated in FIG. 1, is that in the absence of an instrumentality effecting mixing of the water, the warmed water rises and tends to become stratified at the upper portions of the reservoir, with a result of lack of uniformity in the water body. This in turn tends to cause erratic humidification behavior in use of the apparatus.

Pursuant to the present invention a gas inlet/outlet connector 24 is provided, which includes a gas inlet channel 26 which admits incoming dry gas 28 proceeding from a means for supplying gas to a patient such as an anesthesia gas machine, respirator or other gas supply from a hospital central source. The opposed side of connector 24 includes a gas outlet channel 30, from which humidified gas 29 may be furnished to a patient being administered same. Channel 30 is seen to communicate directly with the interior space 32 of chamber 14.

The lower end 34 of connector 24 is seen to include an opening 35 terminating gas inlet channel 26. Secured completely about the circumference of this lower end 34, is an umbrella-shaped member 36. The upper annular rim 38 of such member is secured in gas-tight relationship with connector 24, and the lower peripheral edge 40 resides somewhat beneath the surface 42 of water reservoir 16. The downwardly facing concavity within umbrella-shaped 36 is completely open, and thus it will be evident that surface 42 of the water co-operates with the interior of member 36 to define a gas accumulation space 44.

Figure 2:
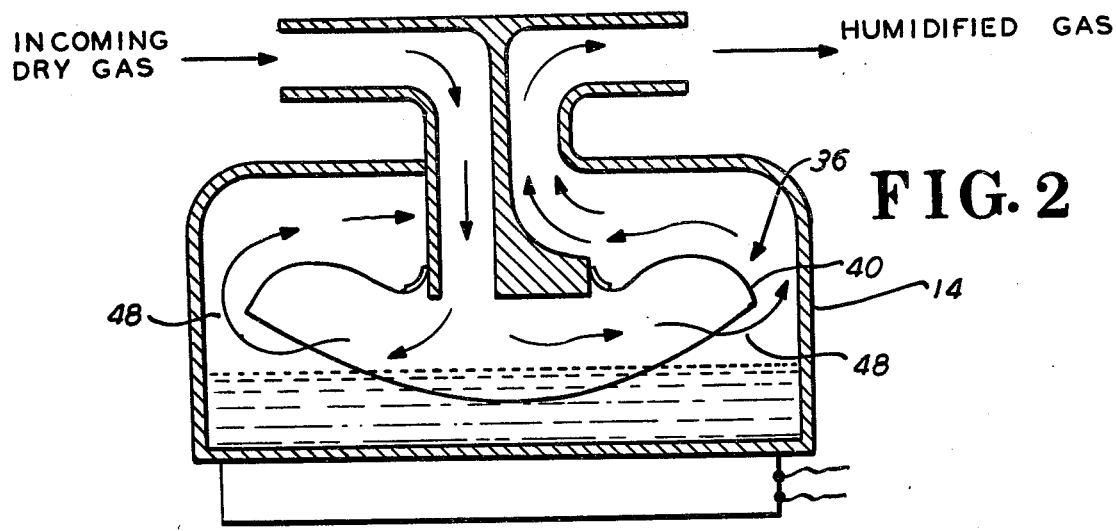
FIG. 2 is a longitudinal cross-sectional view similar to FIG. 1, showing the resulting flexure and consequent gas flow paths occurring in the course of operation of the FIG. 1 apparatus.

In the embodiment of apparatus 10 set forth in FIGS. 1 and 2, connector 24 may be regarded as fixedly secured to chamber 14 at the interface 46 therewith. Thus connector 24 is constrained against vertical displacements; and similarly it will be evident that the rim 38 of member 36 which is attached to connector 24 is similarly constrained against vertical displacements.

On the other hand, the material constituting umbrella-shaped member 36 in the embodiments of FIGS. 1 and 2, is preferably a highly flexible composition as, for example, a polyvinyl chloride or other plastic of relatively thin gauge, or comprises a natural or artificial rubber or the like. In consequence, the said member 36 is characterized as being per se flexible, and portions radially outward from the affixed rim 38, may be displaced, particularly in an upward direction, by forces developed internally of gas accumulations space 44 due to pressure build-up of gas.

The action that thereby occurs in the device 10 as pressure within space 44 increases relative to the pressure in space 32, is depicted in schematic fashion in FIG. 2, wherein it is seen that eventually an elastic deformation takes place wherein one or more portions of the peripheral edge 40 of member 36 are displaced upwardly above the surface 42 of the water—enabling gas within space 46 to suddenly emerge, as is suggested at 48.

It will be appreciated in this connection that the edge where the gas thus emerges, having been just displaced from the water surface 42, has in turn disrupted said surface just prior to gas passage, to effectively provide agitation in the zone of escape, which promotes a close, intimate contact between the emerging gas and the water at such zone. This in turn promotes transfer of water vapor to the emerging gas with high efficiency. In addition, of course, the gas has previously been humidified to a considerable extent during its course of build-up in gas accumulation space 44—since such gas while dwelling in space 44 is in contact with the underlying water surface bordering same.

It should be appreciated in connection with FIG. 2 that the showing therein, as already mentioned, is schematic. The precise mode of deformation of member 36 depends upon the specific degree of flexibility of the material comprising same, and on the gas flow rates, pressure build-up rate, etc. The member 36 can, depending on the foregoing factors, deform so that virtually the entire peripheral edge 40 is simultaneously displaced from the water surface 42 to allow gas flow outwardly in the manner indicated; or alternatively the said member 36 can elastically deform so that one or more portions or sections of peripheral edge 40, are at different times displaced upwardly to permit gas emergence.

The humidified gas thus provided to the space 32 between the external portion of member 36 and the internal wall of chamber 14, thence proceeds through the outlet channel 30 and thence to the patient. As the pressure in the respective spaces 32 and 44 becomes equalized, member 36 (by virtue of its elasticity) is self-restored to its "normal" configuration—as in FIG. 1.

Figure 3:
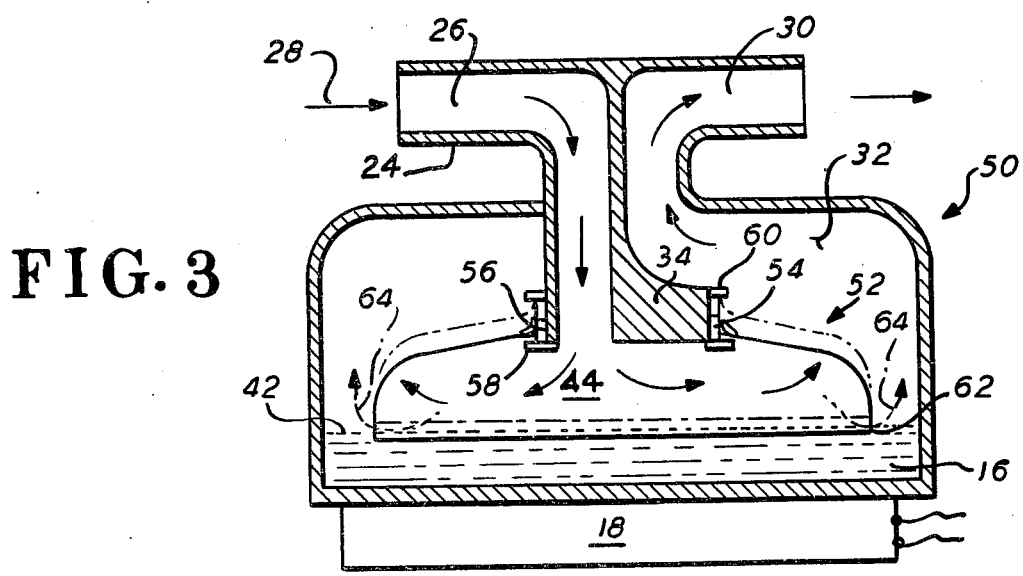
FIG. 3 is a further longitudinal cross-sectional view, illustrating a second embodiment of apparatus in accordance with the present invention; the view also shows the mode of operation of the second embodiment of the invention in the course of operation thereof.

In FIG. 3 herein, a schematic longitudinal cross-sectional view appears, illustrating a further embodiment of apparatus in accordance with the invention. The view of FIG. 3, in analogy to that of FIG. 1, illustrates the apparatus 50 in its "normal" configuration, i.e. prior to build-up of a positive differential pressure under the umbrella-shaped member 52; the view further depicts (in shadow) the action occurring upon the differential pressure reaching a sufficient point to displace member 52 and enable gas escape from space 44.

The apparatus depicted in FIG. 3 is generally similar to that of FIGS. 1 and 2, and corresponding elements are identified by the same reference numerals as are used in the earlier Figures. Whereas, the device of FIGS. 1 and 2 utilizes as member 36 a flexible element which is constrained against unit movement in a vertical direction, but which (by virtue of its flexibility) can be elastically displaced at the radially outward and peripheral portions thereof, the device 50 of FIG. 3 utilizes a member 52 of a relatively rigid material, which, while remaining umbrella-shaped, can comprise a relatively inflexible plastic or the like.

The said member 52 in this instance, is seen to be secured to connector 24 via an annular collar 54 which is mounted about the lower end 34 of connector 24, but by virtue of the loose fit at interface 56 is vertically displaceable in an upward and downward direction. Thus the said collar 54, carrying with it member 52, can move downwardly until reaching the lip 58 formed on the portion 34, or can move upwardly until impinging against the lip 60 also formed on connector 34.

As seen from the solid line depiction of member 52 in FIG. 3, the member 52 normally resides with its lower peripheral edge 62 beneath the surface 42 of water reservoir 16. As incoming dry gas 28 enters the gas accumulation space 44, the differential pressure between such space and space 32 surrounding member 52 increases, and in due course (depending upon the gas flow rate, the material comprising member 52 and so forth) a point will be reached at which member 52 secured to collar 54 moves upwardly (to the dotted line position), permitting the gas to then escape under the peripheral edge 62—as is suggested by the arrows 64. The escaping gas, as was described in connection with the prior embodiment, passes in intimate contact with the disrupted water interface, adding to the humidification effects which to some degree have already been effected within gas accumulation space 44. Thereafter, as already described in connection with FIGS. 1 and 2, the humidified gas proceeds through space 32, and then exits via channel 30 and proceeds toward the patient.

With the pressure in spaces 44 and 32 now approximately equal, the member 36 falls under its own weight, with the collar 54 sliding downwardly with such member; and the configuration illustrated in solid lines in FIG. 3 is restored, with cyclic action of the type discussed thereafter continuing.

It will be appreciated both in connection with the embodiments of FIGS. 1 and 2, and that of FIG. 3, that the materials constituting the members 36 and 52 and (in the case of the embodiment of FIG. 3) the moveable collar 54, can be of very light weight by virtue of their plastic or similar construction; and it will thus be appreciated that the humidification action described, i.e. constituting an intermittent escape of gas under the edge of member 36 or 52, can be brought about by a relatively slight pressure differential occurring as between spaces 44 and 32. The present apparatus thus introduces a relatively low pressure drop in the gas passing therethrough and for such reason—in spite of the simplicity of the present apparatus—actuation thereof can actually be effected and controlled by the patient's breathing. This is to say that even assuming that the gas flow proceeding by a channel 26 is approximately at atmospheric pressure (e.g. by the flow to channel 26 from a gas source being controlled by a suitable regulator valve or the like), actuation of the present device may be brought about by the patient's breathing reducing the pressure within space 32, to thereby generate an adequate pressure differential across spaces 44 and 32 as to enable the actuation shown in FIGS. 2 and 3.

While the present invention has been particularly set forth in terms of specific embodiments thereof, it will be understood in view of the present disclosure, that numerous variations upon the invention are now enabled to those skilled in the art, which variations yet reside within the scope of the present teaching.

For example, in both the embodiment of the invention illustrated in FIGS. 1 and 2, and that illustrated in FIG. 3, gas is introduced into the space 44 via gas inlet channel 26. However, other equivalent means can be used to channel the gas into space 44, including, e.g. a gas delivery tube which can enter chamber 14 from any convenient point and discharge into space 44 from the direction of the underlying reservoir 16.

Accordingly, the invention is to be broadly construed and limited only by the scope and spirit of the claims now appended hereto.

I CLAIM:

1. A gas humidifying apparatus, comprising in combination:
    a generally enclosed chamber adapted to contain a water reservoir;
    a highly flexible umbrella-shaped member mounted in said chamber with the open concavity thereof facing said water reservoir, and with the peripheral edge of said member normally extending beneath said water, whereby the interior of said member defines with said water surface a gas accumulation space;
    gas inlet means communicating with said gas accumulation space for introducing gas to be humidified therein;
    gas outlet means communicating with the chamber space external to said member;
    at least portions of the peripheral edge of said member being upwardly displaceable by a positive pressure differential established in said gas accumulation space with respect to said chamber space in consequence of gas flow between said inlet and said outlet, and said displaced edge portions being self-restorable to said normal position upon said gas pressures being equalized across said accumulation and chamber spaces; whereby the resultant intermittent displacements of said member edge above said water level enables intermittent flow of humidified gas from said accumulation space and through said chamber space to said gas outlet means; said displacements of said peripheral edge from said water serving further to agitate the said water and surface thereof to promote intimate contact between said gas and said water to effect improved humidification of said gas.

2. Apparatus in accordance with claim 1, further including heating means disposed to flow heat into the water at the bottom of said reservoir; said displacements of said umbrella-shaped member further serving by agitation of said water to mix the heated layers of water accumulating at the upper surfaces of said reservoir with the underlying volumes of said water, to thereby promote uniformity in the temperature in said reservoir.

3. A gas humidifying device, comprising:
    a generally enclosed chamber adapted to contain a water reservoir;
    a highly flexible umbrella-shaped member positioned in said chamber with the entire downwardly facing peripheral edge of said umbrella normally extending beneath the surface of said water reservoir, whereby the interior of said umbrella-shaped member defines with said water surface a gas accumulation space in contact with said water surface;
    gas inlet means connected to the interior of said umbrella-shaped member for introducing gas to be humidified into said gas accumulation space;
    gas outlet means connected to said chamber and communicating with the space in said chamber external to said umbrella-shaped member;
    at least portions of the peripheral edge of said umbrella-shaped member being upwardly displaceable from said normal position in response to pressure build-up in said gas accumulation space resulting from gas flow through said gas accumulation space; and said member being restorable to said normal configuration with said entire peripheral edge extending beneath said water surface when the gas build-up in said accumulation space is relieved through said gas outlet means; whereby the resultant intermittent displacements of said umbrella edge above said water level enables periodic flow of humidified gas from said gas accumulation space to said gas outlet means, said periodic displacement of said peripheral edge from said water serving further to agitate said water and surface thereby to promote humidification of said gas.

4. Apparatus in accordance with claim 3, further including heating means disposed to flow heat into the water reservoir; said displacements of said umbrella-shaped member serving by agitation of said water to mix the heated layers of water accumulating at the upper surfaces of said reservoir with the underlying volumes of said water, to thereby promote uniformity in the water temperature in said reservoir.

5. A gas humidifying device, comprising;
    a generally enclosed chamber adapted to contain a water reservoir;

a highly flexible umbrella-shaped member mounted in said chamber with the downwardly facing edge of said umbrella normally extending beneath the surface of said water reservoir, whereby the interior of said member defines with said water surface a gas accumulation space in contact with said water surface;

gas inlet means connected to said member interior, for introducing gas to be humidified into said gas accumulation space;

gas outlet means connected to said chamber and communicating with the chamber space external to said member;

whereby pressure build-up in said gas accumulation space resulting from flow through said inlet and outlet means effects elastic distortion of said umbrella-shaped member with resultant displacement of said umbrella edge above said water level, to thereby enable intermittent flow from said gas accumulation space to said gas outlet means, said periodic displacements further agitating said water and surface thereof to facilitate humidification of gas flowing under said edge and toward said outlet means.

6. Apparatus in accordance with claim 5, further including heating means disposed to flow heat into the water at the bottom of said reservoir; said periodic displacements of said umbrella-shaped member further serving by agitation of said water to mix the heated layers of water accumulating at the upper surfaces of said reservoir with the underlying volumes of said water, to thereby promote uniformity in the temperature in said reservoir.

* * * * *